United States Patent
Bäckström et al.

(10) Patent No.: US 11,026,953 B2
(45) Date of Patent: Jun. 8, 2021

(54) 3-BETA-HYDROXY-5-ALPHA-PREGNAN-20-ONE FOR USE IN TREATMENT OF ESSENTIAL TREMOR

(71) Applicant: ASARINA PHARMA AB, Solna (SE)

(72) Inventors: Torbjörn Bäckström, Umeå (SE); Markus Jerling, Bromma (SE)

(73) Assignee: ASARINA PHARMA AB, Solna (SE)

( * ) Notice: Subject to any disclaimer, the term of this patent is extended or adjusted under 35 U.S.C. 154(b) by 0 days.

(21) Appl. No.: 16/484,920

(22) PCT Filed: Sep. 2, 2018

(86) PCT No.: PCT/SE2018/050118
§ 371 (c)(1),
(2) Date: Aug. 9, 2019

(87) PCT Pub. No.: WO2018/147791
PCT Pub. Date: Aug. 16, 2018

(65) Prior Publication Data
US 2019/0381069 A1 Dec. 19, 2019

(30) Foreign Application Priority Data
Feb. 10, 2017 (SE) .................. 1750124-8

(51) Int. Cl.
*A61K 31/57* (2006.01)
*A61K 45/06* (2006.01)

(52) U.S. Cl.
CPC .............. *A61K 31/57* (2013.01); *A61K 45/06* (2013.01)

(58) Field of Classification Search
CPC ...... A61K 31/57; A61K 2300/00; A61P 25/14
See application file for complete search history.

(56) References Cited

U.S. PATENT DOCUMENTS

| 5,232,917 A | 8/1993 | Bolger et al. |
| 5,939,545 A | 8/1999 | Upasani et al. |

FOREIGN PATENT DOCUMENTS

| EP | 2241628 A1 | 10/2010 |
| JP | 2005-132799 A1 | 5/2005 |
| WO | WO99/45931 A1 | 9/1999 |
| WO | WO03/059357 A1 | 7/2003 |
| WO | WO2008/063128 A1 | 5/2008 |
| WO | WO2016/040322 A1 | 3/2016 |
| WO | WO2016/114655 A1 | 7/2016 |
| WO | WO2016/164763 A1 | 10/2016 |
| WO | WO2016/205721 A1 | 12/2016 |
| WO | WO2017/156103 A1 | 9/2017 |

OTHER PUBLICATIONS

Prince, R. J., et al., "Differential Antagonism by Epipregnanolone of Alphaxalone and Pregnanolone Potentiation of [3H]Flunitrazepam Binding Suggests More Than One Class of Binding Site for Steroids at GABAA Receptors," Neuropharm. 1993;32(1):59-63.

Wang, M.D., et al., "The inhibitory effects of allopregnanolone and pregnanolone on the population spike, evoked in the rat hippocampal CA1 stratum pyramidale in vitro, can be blocked selectively by epiallopregnanolone," Acta Physiol. Scand. 2000;169:333-341.

Wang, M., et al., "3beta-Hydroxypregnane Steroids Are Pregnenolone Sulfate-Like GABAA Receptor Antagonists," J. Neurosci. 2002;22(9):3366-3375.

International Search Report for PCT Patent App. No. PCT/SE2018/050118 (dated Apr. 16, 2018).

*Primary Examiner* — Barbara P Badio
(74) *Attorney, Agent, or Firm* — Cermak Nakajima & McGowan LLP; Malcolm P. McGowan (57) ABSTRACT

The present invention provides the steroid compound 3beta-hydroxy-5alpha-pregnan-20-one for use in treatment of essential tremor, as well as methods for treating essential tremor and pharmaceutical compositions for use in treatment of essential tremor.

7 Claims, 3 Drawing Sheets

3-BETA-HYDROXY-5-ALPHA-PREGNAN-20-ONE FOR USE IN TREATMENT OF ESSENTIAL TREMOR

CROSS-REFERENCE TO RELATED APPLICATIONS

This application is a National Stage Entry of PCT/SE2018/050118, filed Feb. 9, 2018, which claims priority from Swedish patent application 1750124-8, filed Feb. 10, 2017. The contents of these priority applications are incorporated herein by reference in their entirety.

FIELD OF THE INVENTION

The present invention provides the steroid compound 3beta-hydroxy-5alpha-pregnan-20-one for use in treatment of essential tremor, as well as methods for treating essential tremor and pharmaceutical compositions for use in treatment of essential tremor.

BACKGROUND OF THE INVENTION

Essential tremor (ET) typically involves shaking of the arms, hands or fingers and sometimes also involving the head, vocal cords or other body parts during voluntary movements, such as eating and writing. ET is commonly described as an action tremor and it intensifies when one tries to use the affected muscles or postural tremor that is present with sustained muscle tone rather than a resting tremor. ET generally presents as a rhythmic tremor (4-12 Hz) that occurs only when the affected muscle is exerting effort. ET is one of the most common neurological diseases, with a prevalence of approximately 4% in persons aged 40 and older and considerably higher among persons in their 60s, 70s, 80s, and 90s. Physical or mental stress makes the tremor worse as well in response to fatigue, strong emotions, low blood sugar, cold and heat, caffeine, lithium salts, some antidepressants, and other factors. It is typical for the tremor to worsen in "performance" situations, such as when writing or giving a presentation.

The basis for ET according to current knowledge is: There is a pacemaker for oscillatory signal output towards thalamus in the dentate nucleus of the cerebellum. In normal condition, GABAergic input to dentate nucleus from Purkinje cells exerts tonic inhibition on the oscillatory pacemaker in dentate nucleus output neurons. In ET there is a cerebellar dysfunction of Purkinje cells with decrease of their GABAergic function. In ET, dentate nucleus output neurons towards ventrolateral thalamus are disinhibited due to a reduction in GABAergic tonus, leading to unrestrained oscillatory signal through cerebello-thalamo-cortical pathways. Especially the ventrolateral thalamus is involved in the tremor generation.

There are four steps in the pathogenesis of ET. Step 1 involves cerebellar degeneration with change of Purkinje cell function. Step 2 is a consequence of the previous step, activity of the GABA system decreases in deep cerebellar neurons. In step 3, pacemaker activity of deep cerebellar neurons is not inhibited and the signal thus increases in strength. Step 4, the rhythmic activity is transferred to the thalamus and the activity in thalamo-cortical circuit increases and engaging motor neurons causing tremor.

The current opinion is that a treatment with GABA enhancing compounds should be beneficial treatment. Therefore, several studies using different types of GABA enhancers as treatment have been made. However, only modest results have been obtained. Primidone has been shown to be most effective, with a reduction between 35-50% of tremor scores. The positive $GABA_A$ receptor modulator alprazolam gives a reduction of 25% but still significant over placebo. The compound primidone is metabolized into phenobarbital and phenylethylmalonamide. These metabolites have very limited anti-tremor efficacy, and thus primidone itself directly suppress tremor. Alprazolam is a benzodiazepine acting compound via the $GABA_A$ receptor. Alcohol gives a 50% reduction in tremor scores but only during a short period (30 minutes) with a rebound later.

In imaging PET studies using $^{11}C$-flumazenil a significant increase in binding of $^{11}C$-flumazenil at the benzodiazepine receptor site of the $GABA_A$ receptor is found in the cerebellum, the ventrolateral thalamus, and the lateral premotor cortex of the ET group. The clinical tremor scale scores and parametric binding potential images of $^{11}C$-flumazenil PET, correlated with patients at different stages of clinical severity. This result indicates that there is an increased sensitivity to GABAergic stimulus in the cerebellar-thalamo-cortical pathway generating the tremor. This is puzzling as post-mortem studies show a 35% reduction in $GABA_A$ receptors in the dentate nucleus of the cerebellum from individuals with ET, compared with controls. The $GABA_A$ receptor density was assessed with $^3H$-flunitrazepam allosteric binding to the alpha1 and gamma2-interface (benzodiazepine site) of the $GABA_A$ receptor on cerebellum sections. Thus the study did not investigate extra-synaptic receptors containing the delta subunit. Under normal situations in situ hybridization, histochemistry and quantitative real-time PCR data show that deep cerebellar nuclei neurons mainly express the alpha1, alpha2, beta2 and gamma2 receptor subunits messenger RNAs and the data above show that at least the alpha1 receptor subtypes is reduced in ET. It is a known pharmacological principle that when a pre-synaptic neuronal signal is too low this will be compensated by an up-regulation of the postsynaptic receptor. It seems thus that other types of receptor subunits than alpha1 are up-regulated. The discrepancy between PET using $^{11}C$-flumazenil and binding studies, $^3H$-flunitrazepam could be explained by the fact that delta subunit-containing receptors are shown to bind flumazenil with high affinity, contrary to the widely held belief, these receptors containing delta are insensitive to classical benzodiazepines but binds flumazenil. The classic benzodiazepines like diazepam and flunitrazepam cannot bind to delta subunit containing receptors but to gamma containing receptors. The flumazenil results above combined with the autopsy data would thus indicate an up-regulation of delta subunit containing $GABA_A$ receptors. We know that delta subunit is only present in extra-synaptic $GABA_A$ receptors and is preferably combined with the alpha4 subunit. The above results thus indicate that there is an upregulation of the alpha4,beta,delta sub-receptor form. The alpha4,beta,delta receptor is known to be super sensitive to allopregnanolone enhancement and in this patent application we also show that it is very sensitive to androstandiol a metabolite to testosterone. Naturally produced allopregnanolone and androstandiol will thus easily enhance the severity of the tremor symptoms in the disorder essential tremor. With above information an inhibition of the alpha4, beta,delta receptor would thus be a treatment of the symptoms in essential tremor.

The metabolites of the sex and stress hormones pregnenolone, progesterone, deoxycorticosterone, cortisone and cortisol, known as pregnanolones, as well as the metabolites of testosterone, androstandione and dehydroepiandrosterone, known as androstanes, have all been the subject of various studies, at least partially elucidating their role in the neurological signal system in mammals. The harmful steroids inducing CNS symptoms and disorders of interest in the present application all have a structural similarity in comprising a 3alpha-hydroxy group, a Δ4-pregnene or a 5alpha or 5beta pregnane steroid body, and a ketone or hydroxy group on position 17, 20 or 21.

Steroids comprising 3alpha-hydroxy-5alpha/beta-pregnan/Δ4-pregnen-20-one/ol or 3alpha-hydroxy-5alpha/beta-androstan/Δ4-androsten-17-one/ol have been shown to be important specific enhancers of the $GABA_A$ receptor. They bind to the $GABA_A$ receptor and act by enhancing the effect of GABA in terms of prolonging the $GABA_A$ receptors opening duration. The receptors are of several subtypes located to different areas of the brain and related to different CNS disorders and symptoms. The receptor subtype alpha6, beta,delta is localized in the cerebellum and subtype alpha4, beta,delta is localized in thalamus one of the probable sites of dysfunction of the therapeutic action. In addition, some receptors are localized within a synapse (intra-synaptic) while others are located outside a synapse (extra-synaptic). $GABA_A$ receptor modulating steroids can by themselves in physiological concentrations open the extra-synaptic $GABA_A$ receptor alone (tonic inhibition) but not the intra-synaptic receptors but enhance the effect of GABA itself (phasic inhibition). These two types of effects are dependent on different mechanisms and binding sites on the $GABA_A$ receptor and the effects depends in addition on the subunit composition of the receptor. The receptor subtypes alpha4, beta,delta and alpha6,beta,delta are extra-synaptic subtypes with both tonic and phasic effects of 3alpha-hydroxy-5alpha/beta-pregnan-20-one/ol and 3alpha-hydroxy-5alpha/beta-androstan-17-one/ol. No specific $GABA_A$ modulating steroid antagonists acting on both binding sites or only inhibits one of the mechanisms are known today among persons skilled in the art. The effect of 3alpha-hydroxy-5alpha/beta-pregnan-20-one/ol or 3alpha-hydroxy-5alpha/beta-androstan-17-one/ol is similar to the effects of both benzodiazepines and barbiturates, i.e. they are all positive $GABA_A$ receptor modulators. Said steroid compounds, however, have a binding site separate from that of both these compounds.

U.S. Pat. Nos. 5,232,917 and 5,939,545 disclose a number of 3alpha-hydroxy steroids. These disclosures concern the agonistic modulation of the $GABA_A$ receptor. In other words, the disclosures are both focused on the benzodiazepine-like effect of the 3alpha-hydroxy-5alpha/beta-steroids. All steroids that are positive modulators of the $GABA_A$ receptor have the common feature of a 3alpha-hydroxy structure. Steroids with only a 3beta-hydroxy structure have never been shown to possess a $GABA_A$ receptor positive modulating effect. In all cases where an effective $GABA_A$ receptor-modulating effect is noticed, the steroid has a 3alpha-hydroxy group.

WO 99/45931 discloses a $GABA_A$ modulating steroid antagonist, namely 3beta-hydroxy-5alpha-pregnan-20-one but does not mention anything about the effect in different receptor subtypes e.g. the alpha4,beta,delta subtype and does not disclose 3beta-hydroxy-5alpha-pregnan-20-one effects on phasic or tonic 3alpha-hydroxy-5alpha/beta-steroid activity in intra- or extra-synaptic receptors. The $GABA_A$ modulating steroid antagonist effect of 3beta-hydroxy-5alpha-pregnan-20-one against 3alpha-hydroxy-5alpha/beta-pregnan-20-one was first disclosed by Wang et al. (Wang M. D., Bäckström T. and Landgren S. (2000) Acta Physiol Scand 169, 333-341). In that disclosure, a dose dependent antagonistic effect of 3beta-hydroxy-5alpha-pregnan-20-one on two of the 3alpha-hydroxy-5alpha/beta-steroids was shown. This document does not mention the possibility to use 3beta-hydroxy-5alpha-pregnan-20-one against disorders caused by androgenic $GABA_A$ receptor modulating steroids and the possibility to use 3beta-hydroxy-5alpha-pregnan-20-one as inhibitor at the alpha4,beta,delta activated $GABA_A$ receptor and does not disclose 3beta-hydroxy-5alpha-pregnan-20-one effects on phasic or tonic 3alpha-hydroxy-5alpha/beta-steroid activity in intra- or extra-synaptic receptors.

WO 03/059357 discloses the use of certain pregnane steroids in the treatment of CNS disorders. This document does not mention the possibility to use 3beta-hydroxy-5alpha-pregnan-20-one against disorders caused by androgenic $GABA_A$ receptor modulating steroids and the possibility to use 3beta-hydroxy-5alpha-pregnan-20-one as inhibitor at the alpha4,beta,delta activated $GABA_A$ receptor and does not disclose 3beta-hydroxy-5alpha-pregnan-20-one effects on phasic or tonic 3alpha-hydroxy-5alpha/beta-steroid activity in intra- or extra-synaptic receptors.

3beta steroids can also have effects on the GABA's own effect as disclosed by Wang et al. (The Journal of Neuroscience, May 1, 2002, 22(9):3366-3375). In this disclosure, the authors show that when maximal stimulation of $GABA_A$ receptors is made with GABA, certain 3beta-hydroxypregnane steroids are able to inhibit GABA's own effect. But that certain 3beta-hydroxy steroids would mainly inhibit GABA steroid effects on GABA gated chloride flux and other steroids would also inhibit GABA's own effect was not discovered. This document does not mention the possibility to use 3beta-hydroxy-5alpha-pregnan-20-one against disorders caused by androgenic $GABA_A$ receptor modulation steroids and the possibility to use 3beta-hydroxy-5alpha-pregnan-20-one as inhibitor at the alpha4,beta,delta activated $GABA_A$ receptor and does not disclose 3beta-hydroxy-5alpha-pregnan-20-one effects on phasic or tonic 3alpha-hydroxy-5alpha/beta-steroid activity in intra- or extra-synaptic receptors. WO2008/063128 discloses the use of certain pregnane steroids in the treatment of CNS disorders. WO2008/063128 does not mention the possibility to use 3beta-hydroxy-5alpha-pregnan-20-one against disorders caused by androgenic $GABA_A$ receptor modulating steroids and the possibility to use 3beta-hydroxy-5alpha-pregnan-20-one as inhibitor at the alpha4,beta,delta activated $GABA_A$ receptor and does not disclose 3beta-hydroxy-5alpha-pregnan-20-one effects on phasic or tonic 3alpha-hydroxy-5alpha/beta-steroid activity in intra- or extra-synaptic receptors.

It remains a challenge to find specific antagonists of the 3alpha-hydroxy-androstan/pregnane action on the $GABA_A$ receptor that have an activity on alpha4,beta,delta subtype and low inhibitory effects on GABA itself. In addition to find compounds that are physiologically safe and suitable for pharmaceutical use, and which additionally are applicable in physiologically acceptable doses with reasonable time intervals.

One objective of the present invention is thus to identify such specific blockers active against both 3alpha-hydroxy-androstan/androsten-steroids and 3alpha-hydroxy-pregnane/pregnene-steroids, and have effects on phasic and/or tonic 3alpha-hydroxy-5alpha/beta-steroid activity in intra- or extra-synaptic receptors, and especially on the alpha4,beta, delta subtype, and to make available novel pharmaceuticals and methods for the treatment, alleviation or prevention of ET. Further objectives, the associated solutions and their advantages follow with the description, examples and claims.

DESCRIPTION OF THE INVENTION

The neuronal activity in the brain is decreased when the $GABA_A$ receptor is open and a large amount of chloride flux into the cell. It is also known that there is a relation between the amount of chloride moving in and the clinical effect of a $GABA_A$ receptor active drug. It is also known that $GABA_A$ receptors with different subunit composition reacts differently on 3alpha-hydroxy-delta 4-5, 5alpha/beta-steroids but there is no prior knowledge on how 3beta-hydroxy-5alpha-pregnan-20-one will act on different receptor subtypes e.g. alpha4,beta,delta receptor subtype or what effects 3beta-hydroxy-5alpha-pregnan-20-one will have on phasic or tonic 3alpha-hydroxy-5alpha/beta-steroid activity in intra- or extra-synaptic receptors or if 3beta-hydroxy-5alpha-pregnan-20-one can antagonize 3alpha-hydroxy, 5 alpha-androstane/androstene steroids.

The delta subunit is only present in extra-synaptic $GABA_A$ receptors. In cerebellum the extra-synaptic receptor type is mainly the alpha6,beta,delta but highly relevant and interesting is that in thalamus the extra-synaptic subtype is preferably alpha4,beta,delta. Both these receptor subtypes containing delta are hypersensitive to alcohol and that could explain the therapeutic effect of low doses of alcohol in ET. Tonic conductance mediated by extra-synaptic $GABA_A$ receptors has been implicated in the modulation of network oscillatory activity. A low concentration of the benzodiazepine site agonist, zolpidem, reduced the power of oscillatory activity. By contrast, higher doses augmented the activity.

Extra-synaptic $GABA_A$ receptors have been implicated in the modulation of network oscillatory activity. A low concentration of $GABA_A$ receptor agonists, reduced the power of oscillatory activity. By contrast, higher doses augmented the activity. Based on the above reasoning it is surprising that the most logical treatment would be to inhibit the low stimulation instead of trying to increase the GABA action. Treatments trying to increase the GABA action have limited success (see above) but to inhibit GABA action is surprising.

As a conclusion the data indicates that the reduced GABAergic release and function gives a compensatory up-regulation of the extra-synaptic alpha4,beta3,delta containing $GABA_A$ receptor. This receptor subtype is the subject of biphasic modulation by $GABA_A$ receptor activators. Low but increased GABA concentration reduce the inhibitory effect on the oscillating neurons in the dentate nucleus of the cerebellum compared to no GABA release while high concentrations increased the inhibitory effect on the oscillating neurons in the of dentate nucleus. There is thus two ways to treat the dysfunction 1) by inhibiting the low but increased GABA activation or 2) to increase the activity in the GABA stimulation so an inhibition of the oscillations would be inhibited. This second way of treatment has been tried (see above) with limited success but the first treatment possibility is new and surprising and has never been tested.

In one aspect, the present invention provides 3beta-hydroxy-5alpha-pregnan-20-one, for use in treatment of essential tremor.

In one embodiment of this aspect, there is provided 3beta-hydroxy-5alpha-pregnan-20-one, for said use, in combination with at least one active compound, selected from anti-convulsant drugs including primidone, topiramate and phenobarbital; adrenergic blockers including propranolol, atenolol, nadolol, metoprolol and timolol; alcohol derivates including R-baclofen, clonazepam, alprazolam, gabapentin, pregabalin, nimodipine, clozapine, olanzapine and botulinum toxin A; and in combination with surgical interventions including deep brain stimulation.

In one aspect, the present invention provides use of 3beta-hydroxy-5alpha-pregnan-20-one, in the preparation of a medicament useful in the treatment of essential tremor.

In one embodiment of this aspect, said use is provided in combination with at least one active compound, selected from anti-convulsant drugs including primidone, topiramate and phenobarbital; adrenergic blockers including propranolol, atenolol, nadolol, metoprolol and timolol; alcohol derivates including R-baclofen, clonazepam, alprazolam, gabapentin, pregabalin, nimodipine, clozapine, olanzapine and botulinum toxin A; and in combination with surgical interventions including deep brain stimulation In one aspect, the present invention provides a method of treating, preventing or alleviating essential tremor, comprising administering a pharmaceutically effective amount of 3beta-hydroxy-5alpha-pregnan-20-one, to a patient in need thereof.

In one embodiment of this aspect, said method is provided in combination with at least one active compound, selected from anti-convulsant drugs including primidone, topiramate and phenobarbital; adrenergic blockers including propranolol, atenolol, nadolol, metoprolol and timolol; alcohol derivates including R-baclofen, clonazepam, alprazolam, gabapentin, pregabalin, nimodipine, clozapine, olanzapine and botulinum toxin A; and in combination with surgical interventions including deep brain stimulation.

In one aspect, the present invention provides a pharmaceutical composition comprising 3beta-hydroxy-5alpha-pregnan-20-one, for use in treatment of essential tremor, together with pharmaceutically acceptable carriers, excipients and/or diluents.

3beta-hydroxy-5alpha-pregnan-20-one possesses a hydrogen donor in 3beta position, in the form of a hydroxy group that surprisingly function as efficient blocker of the 3alpha-hydroxy-pregnane/pregnene-steroid action at the $GABA_A$ receptor subtype alpha1,beta,gamma but act differently on the alpha4,beta,delta subtype and can antagonize actions of 3alpha-hydroxy-androstane/androstene-steroids being positive $GABA_A$ receptor modulator. 3beta-hydroxy-5alpha-pregnan-20-one thus has utility as therapeutic substance for the prevention and/or treatment of ET and other related androgen/pregnene-induced CNS disorders.

One aspect of the present invention is the therapeutic use of the above compound as blocking substances against the 3alpha-hydroxy-pregnan-steroid action on the alpha4,beta,delta $GABA_A$ receptor subtype and action on androgen metabolites active on the $GABA_A$ receptor. In addition, these substances are now suggested for the manufacture of pharmaceuticals for the treatment of ET or related steroid induced CNS disorders and for use in methods of treatment, according to the attached claims, which are incorporated herein by reference.

One aspect of the present invention relates to the effects 3beta-hydroxy-5alpha-pregnan-20-one have on phasic and tonic 3alpha-hydroxy-5alpha/beta-pregnane/pregnene-steroid activity or 3alpha-hydroxy-5alpha/beta-androstane/androstene-steroid activity in intra- or extra-synaptic receptors. 3beta-hydroxy-5alpha-pregnan-20-one thus has utility as therapeutic substance for the prevention and/or treatment of essential tremor and other related androgene/pregnene induced CNS disorders.

The compound can be used alone or as prodrugs and/or in combination with formulations and other compositions in order to enhance and modulate the effects on CNS. Compositions within the scope of this invention include all compositions wherein the compounds of this invention are contained in an amount that is effective to achieve the intended purposes.

The present inventors have identified that 3beta-hydroxy-5alpha-pregnan-20-one compound possesses a surprising function as efficient blockers of the 3alpha-hydroxy-androstane/pregnane action but is minimally active against GABA itself on the alpha4,beta,delta $GABA_A$ receptor subtype. 3beta-hydroxy-5alpha-pregnan-20-one has thus utility as therapeutic substance for the prevention and/or treatment of ET.

Before the present invention is described, it is to be understood that the terminology employed herein is used for the purpose of describing particular embodiments only and is not intended to be limiting, since the scope of the present invention will be limited only by the appended claims and equivalents thereof.

In particular, it must be noted that, as used in this specification and the appended claims, the singular forms "a", "an", and "the" also include plural referents unless the context clearly dictates otherwise.

The term "blocking" is meant to define an effect where in this case the 3alpha-hydroxy-5alpha/beta-steroids are prevented from acting on the $GABA_A$ receptor. It is understood that "blocking" is an entirely different effect than meant by "modulation" or "repression" or similar terms, which suggest that an action is still taking place, but to a lesser extent or at a slower rate.

The term "pharmaceutical composition" is used in its widest sense, encompassing all pharmaceutically applicable compositions containing at least one active substance, and optional carriers, adjuvants, constituents etc. The term "pharmaceutical composition" also encompasses a composition comprising the active substance in the form of derivate or a prodrug, such as pharmaceutically acceptable salts, sulphates and esters. The manufacture of pharmaceutical compositions for different routes of administration falls within the capabilities of a person skilled in galenical chemistry.

The phrase "UC1010" denotes the compound 3beta-hydroxy-5alpha-pregnan-20-one.

The terms "administration" and "mode of administration" as well as "route of administration" are also used in their widest sense. The pharmaceutical composition of the present invention may be administered in a number of ways depending largely on whether a local, topical or systemic mode of administration is most appropriate for the condition be treated. These different modes of administration are for example topical (e.g., on the skin), local (including ophthalmic and to various mucous membranes such for example nasal, buccal, vaginal and rectal delivery), oral or parenteral and pulmonary, including the upper and lower airways.

The preparation of such compositions and formulations is generally known to those skilled in the pharmaceutical and formulation arts and may be applied to the formulation of the composition of the present invention.

The invention concerns 3beta-hydroxy-5alpha-pregnan-20-one, with surprising blocking effect of 3alpha-hydroxy-5alpha/beta-pregnan-20-one/ol, 3alpha-hydroxy-delta 4-5-pregnene-20-one/ol, on 3alpha-hydroxy-5alpha-androstan-17-ol/one and on 3alpha-hydroxy-delta 4-5-androsten-17-ol/one effects on the $GABA_A$ receptor subtype alpha4,beta,delta and thereby exerts a surprising therapeutic effect on ET and other 3alpha-hydroxy-delta 4-5,/5alpha/beta-steroid induced CNS disorders. The present invention arises out of the surprising finding that 3beta-hydroxy-5alpha-pregnan-20-one has an effect on the alpha4,beta,delta $GABA_A$ receptor subtype as an antagonist to positive modulators of the GABA receptor signaling.

The terms "steroid related" or "steroid induced" are meant to encompass the three possible mechanisms by which steroids act on the central nervous system: a) direct action, b) tolerance induction, and c) withdrawal effect.

The term "3beta-hydroxy-5alpha-pregnan-20-one" equals to "UC1010".

The present inventors have surprisingly identified that 3beta-hydroxy-5alpha-pregnan-20-one in pharmaceutically suitable and practically applicable doses can block the action of both 3alpha-hydroxy-pregnane and androstane steroids on the human $GABA_A$ receptor expressed in HEK-294 cells in vitro, thus blocking the development of the negative effects of 3alpha-hydroxy-pregnane and androstane steroids. In addition the present inventors have surprisingly shown that 3beta-hydroxy-5alpha-pregnan-20-one in pharmaceutically suitable and practically applicable doses can block the action of 3alpha-hydroxy-pregnane and androstane steroids on the human alpha4,beta,delta $GABA_A$ receptor subtype expressed in HEK-294 cells in vitro, thus blocking the development of the negative effects in CNS areas related to cerebello-thalamo-cortical pathway being the main $GABA_A$ receptor subtype involved in the pathogenesis of ET. Both the mechanism of action in ET by action of 3alpha-hydroxy-delta 4-5, 5alpha/beta-steroids particular androstane steroids, the mechanism of action at the alpha4,beta,delta subtype of $GABA_A$ receptor and the effect on phasic and tonic modulation of the $GABA_A$ receptor subtypes including alpha1 and alpha4 in pharmacological acceptable dosages have been addressed.

The present invention further concerns a method for the treating, preventing or alleviating essential tremor in human patients described above, according to which method 3beta-hydroxy-5alpha-pregnan-20-one is administered to said patient. Suitable routes of administration are for example the following: intravenous, nasal, buccal, vaginal, rectal, subcutaneous, percutaneous and oral administration. Percutaneous administration, using the substances formulated as a cream, a gel, and an ointment or in the form of slow-release adhesive medicine patches, is another possible form of administration. In any of these or other routes of administration, the formulation of the composition may be adapted or adjusted according to normal pharmacological procedures, comprising the effective pharmaceutical in a chemical form, suitable for the chosen route, together with suitable adjuvants and vehicles, conventionally used and well-known to a person skilled in the art.

Exacerbation of ET caused by long time (days) exposure to 3alpha-hydroxy-5alpha/beta-steroids after stress. According to the present invention, these conditions or symptoms can be prevented, alleviated or treated by the administration of 3beta-hydroxy-5alpha-pregnan-20-one to the patient.

One embodiment of the invention, addressing a problem afflicting women with essential tremor, is menstrual cycle linked increased frequency and/or change in difficulties and a method for the treatment in human patients, according to which method 3beta-hydroxy-5alpha-pregnan-20-one is administered to said patient.

In general, the present invention encompasses the use of 3beta-hydroxy-5alpha-pregnan-20-one, either alone or in combination with other pharmaceuticals, for the manufacture of a pharmaceutical for the treatment or prevention of any one of the 3alpha-hydroxy-delta 4-5, 5alpha/beta-steroid related or induced disorders described in the specification, and especially ET.

The invention will be further described in the following, non-limiting examples.

EXAMPLE 1

Assay for testing $GABA_A$ receptor effects of 3beta-hydroxy-5alpha-pregnan-20-one on human alpha1,beta,gamma and alpha4,beta,delta $GABA_A$ receptor subtype.

Aim: To investigate the effect of 3beta-hydroxy-5alpha-pregnan-20-one on 1) $GABA_A$ receptor function in the absence and presence of GABA and 2) in absence and in presence of the positive $GABA_A$ receptor modulating steroids Tetrahydrodeoxycorticosterone (THDOC) and 3alpha-hydroxy-5alpha-androstan-17-ol (3alpha-OH-adiol) by the Dynaflow™ system on HEK-293 cells. In these tests the protocol was optimized to be similar to the physiological conditions in the synaptic cleft.

Cell culture: HEK-293 cells, permanently transfected with the human alpha1,beta,gamma and alpha4,beta,delta $GABA_A$ receptor subtypes, were seeded at a density of $3 \times 10^4/25$ cm$^2$ in cellbind culture flask. The transfected cells were used for patch-clamp experiments 3 days after seeding. When using the cells for patch-clamp experiments the cells were washed twice with oxygen-bubbled extracellular (EC) solution (see below). About 5 mL EC was then added and the cells were kept in the incubator for about 15 minutes. After 15 minutes the cells came loose from the bottom of the flask and were separated by carefully sucking couple of times with a Pasteur pipette.

DYNAFLOW™ system with Resolve chip was used for patch-clamp experiments: The electrophysiological recordings from HEK-293 cells were performed under voltage-clamp conditions using patch-clamp technique and the DYNAFLOW™ system (DYNAFLOW™ Pro II Platform Zeiss Axiovert 25; Cellectricon AB, Sweden) with Resolve chips as application system.

Patch pipettes were pulled from borosilicate glass and polished to a resistance 2-5 MΩ when filled with suitable intracellular solution (IC) (pH was adjusted to 7.2) and immersed in bath solution (extracellular, EC) (pH is adjusted to 7.4). The recordings were made using an Axopatch 200B amplifier, a Digidata 1322A (Axon instruments, Foster city, USA). Data were acquired using the pCLAMP software sampled at 10 kHz, filtered at 2-10 kHz and analyzed with Clampfit (versions 9.0, both from Axon instruments, Foster city, USA). No higher series resistance than 20 MΩ between pipette and cell membrane was accepted. No series resistance compensation was used. The stability of series resistance was monitored repeatedly from the time course of capacitative transients during the experiments. The measured liquid-junction potential between EC and IC was subtracted in all data presented. An experiments were performed at room temperature (21-23° C.).

Steroids and GABA: GABA was dissolved in EC-solution by ultra sound for about 40 minutes to the concentration of 10 mM in room temperature. All steroids were dissolved to the concentration of 6 mM in DMSO. The DMSO concentration was 0.1% in all end-solutions, including the wash solution (EC) and the solution with GABA alone. End solutions were the solutions added into the wells of the chip.

Electrophysiology: After compensating for the liquid junction potential a steady holding potential of $-17$ mV was used in all experiments. In physiological conditions the HEK-293 had a resting potential at $-40$ mV and a low concentration of chloride ions inside the cell. By using the holding potential of $-17$ mV and the intracellular solution with low chloride ion concentration the chloride ions flux into the cell when the receptors were activated.

Protocol

GABA applications: By using the DYNABLOW™ equipment it was possible to study transfected HEK-293 during almost physiological conditions. The DYNA-FLOW™ system allowed application of solutions for as short as 40 ms up to minutes in time. Physiologically, in the synaptic cleft, GABA was released in mM range for about 2 ms. In these experiments we apply GABA±steroid for 40 ms. It was found that in almost all cells, the first GABA application gave a smaller response than the second GABA application, There was no difference in response between the second and the third GABA application. Therefore, the first GABA application was always repeated twice and the second response was used in the analysis.

Washout: GABA is quite soluble in water and easy to washout from the receptor. The washout time was set to 1 minute after application with GABA solely. Steroids on the other hand were difficult to dissolve in water and also difficult to washout from the receptor. In the experiments, THDOC and 3alpha-OH-adiol were used as the positive $GABA_A$ receptor modulating steroids. With 2 minutes washout time, 200 nM THDOC and 3alpha-OH-adiol was completely washed out as shown by neither an accumulative nor a desensitization effect.

Incubation: To see the effect of the steroids and to achieve stable results it was found that the steroids had to be incubated on the receptor before application of GABA. Different incubation times were studied to achieve the optimal time for attain stable results and minimize the washout time. Incubation time of 20 seconds showed to be the optimal time for washout time of 2 minutes.

EXAMPLE 2

Biological evaluation—HEK-293 cells, permanently transfected with human alpha1,beta,gamma and alpha4,beta,delta $GABA_A$ receptor subtypes and expressing these $GABA_A$ receptors.

Cell lines permanently expressing a functional human $GABA_A$ receptor was made in following steps. The $GABA_A$ receptor subunits alpha1,beta2,gamma2L or alpha4,beta3, delta including introduced Kozac sequences just before the start codons were subcloned into mammalian expression vectors containing Geneticin, Hygromycin B, and Zeocin resistance, respectively. A HEK-293 cell line stably expressing the three $GABA_A$ receptor subunits was produced by transfection of the subunits one at a time. The transfection was followed by selection with the appropriate antibiotics, cell separation with the use of subunit specific antibodies, and production of single cell colonies. Produced cell lines were analysed with immunocytochemistry for the three $GABA_A$ receptor subunits, followed by selection of a suitable cell line showing for the $GABA_A$ receptor normal and good reactivity towards GABA, THDOC and 3alpha-OH-adiol. The $EC_{75}$ was calculated for THDOC and androstandiol and was used as enhancer of GABA when studying the effect of 1 µM UC1010.

Figure 1:
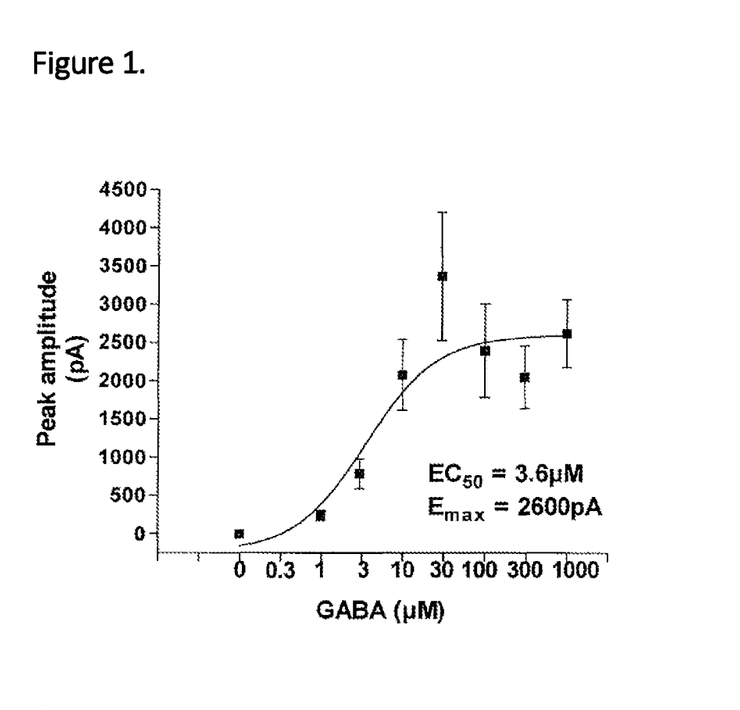
FIG. 1 shows that GABA increased the current response in a concentration-dependent way providing that the receptor alpha1,beta2,gamma2 had a normal and good response.
Figure 2:
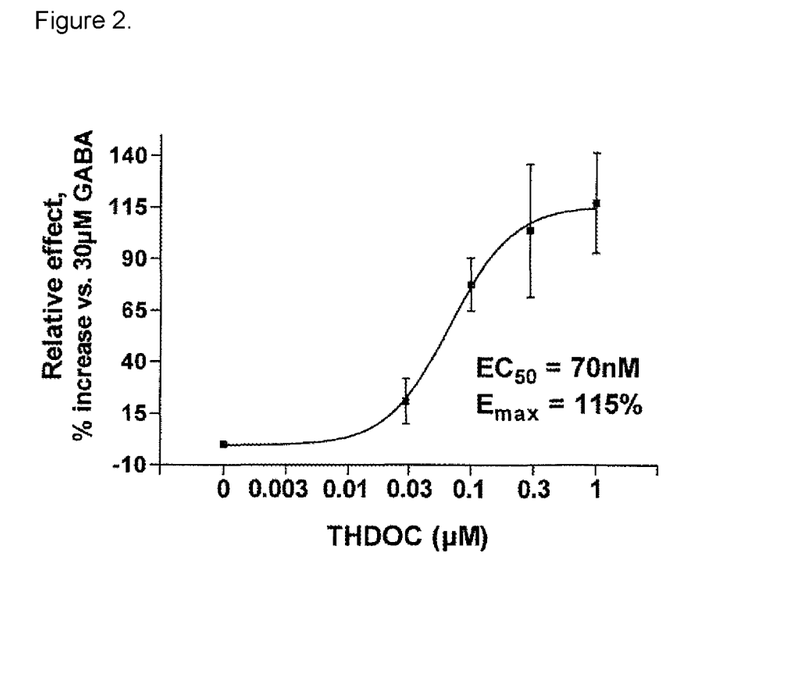
FIG. 2 shows that THDOC enhanced GABA mediated current response in a concentration-dependent way.

Results from tests of GABA in human $GABA_A$ receptor subtype alpha1, beta2, gamma2, permanently expressed in HEK-293 cells are presented in FIG. 1 and FIG. 2. FIG. 1 shows that GABA (1-1000 µM) increased the current response in a concentration-dependent way providing that the receptor alpha1,beta2,gamma2 had a normal and good response. FIG. 2 shows that THDOC (30-1000 nM) enhanced GABA mediated current response in a concentration-dependent way. Control=30 µM GABA, was set to 0 (zero). The figure shows that the receptor alpha1,beta2, gamma2 had a normal and good response.

TABLE 1

THDOC alone significantly induced current response in absence of GABA at alpha4, beta3, delta receptor.

| THDOC (µM) Baseline shift | Mean ± SEM pA (N; P) |
|---|---|
| 0.03 | +5 ± 3.3 pA (N = 9; P = 0.008) |
| 0.1 | +15 ± 9.5 pA (N = 9; P = 0.003) |
| 0.3 | +12 ± 7.9 pA (N = 9; P = 0.019) |
| 1 | +69 ± 35 pA (N = 3; P = 0.018) |

Figure 3:
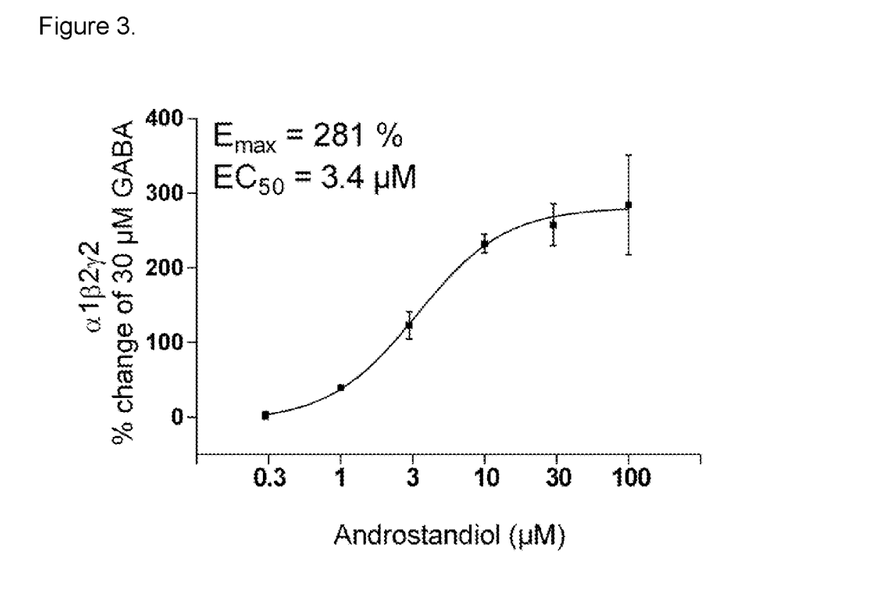
FIG. 3 shows that androstandiol enhanced 30 μM GABA mediated current response at the alpha1,beta2,gamma2 human $GABA_A$ receptor sub type.

FIG. 3 shows that androstandiol (0.3-100 µM) enhanced 30 µM GABA mediated current response at alpha1,beta2, gamma2 human $GABA_A$ receptor sub type. The results in FIG. 3 show surprisingly that androstandiol was substantially less potent (48 times) than THDOC (FIG. 2) in enhancing the effect of GABA on the alpha1,beta2,gamma2 subunit receptor.

TABLE 2

Androstandiol (8-100 µM) induced current response in absence of GABA at alpha1, beta 2, gamma2 receptor.

| Androstandiol (µM) effect by itself (Baseline shift) | Mean ± SEM pA (N; P) |
|---|---|
| 3 | +8 ± 3.6 pA (N = 11; P = 0.004) |
| 8 | +13 ± 2.3 pA (N = 10; P = 0.005) |
| 10 | +11 ± 1.5 pA (N = 10; P = 0.000) |
| 30 | +24 ± 6.8 pA (N = 4; P = 0.001) |
| 100 | +43 ± 5.7 pA (N = 4; P = 0.001) |

Test of GABA in human GABA-A receptor subtype alpha4, beta3,delta permanently expressed in HEK-293 cells.

The recombinant human alpha4,beta3,delta $GABA_A$ receptor showed expected and normal concentration response curve to GABA (data not shown). Further, 1 µM UC1010 GABA-mediated current response was without any significant effect on GABA alone at alpha4,beta3,delta $GABA_A$ receptor subtypes (data not shown).

Figure 4:
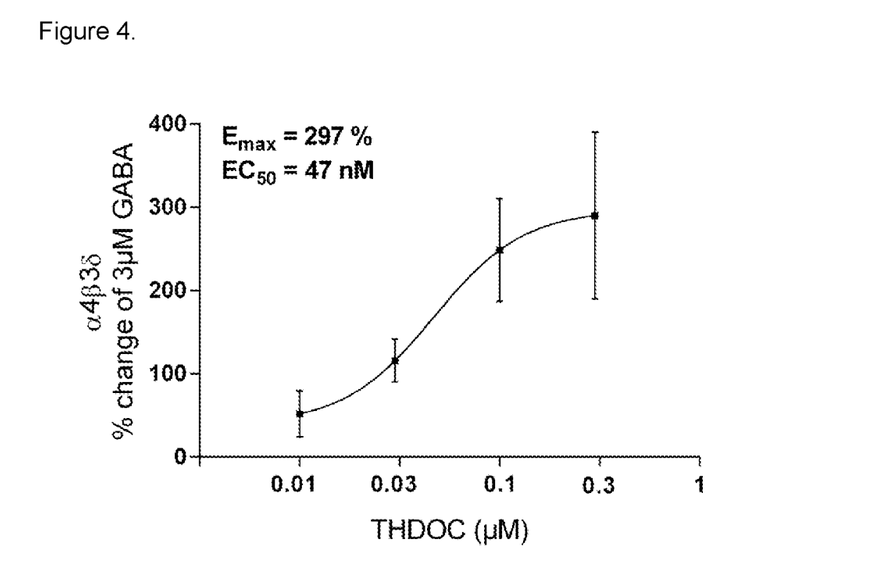
FIG. 4 shows that THDOC enhanced 3 μM GABA-mediated current in a concentration dependent way at the alpha4,beta3,delta human $GABA_A$ receptor sub type.

FIG. 4 shows that THDOC (0.01-0.3 µM) enhanced 3 µM GABA-mediated current in a concentration dependent way at alpha4,beta3,delta receptor.

Figure 5:
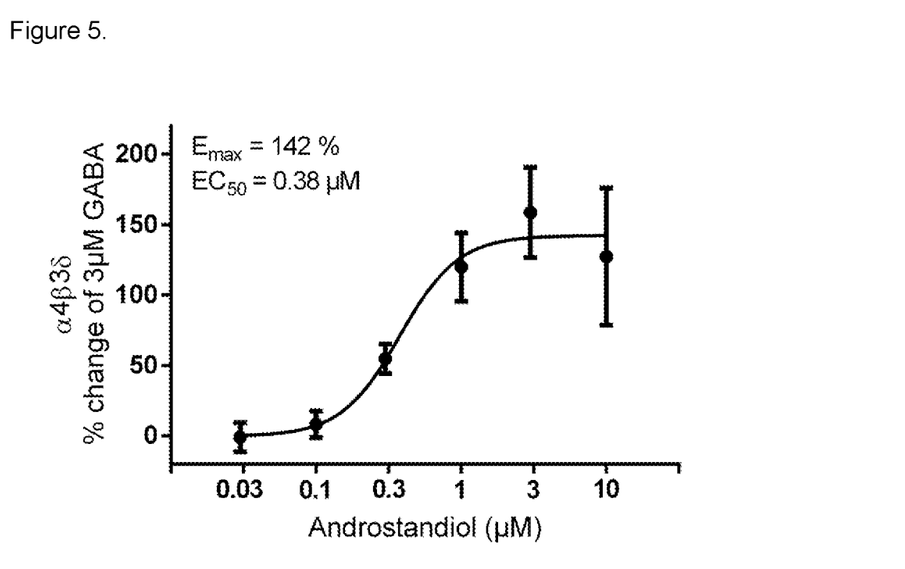
FIG. 5 shows that androstandiol enhanced 3 μM GABA-mediated current response at the alpha4,beta3,delta human $GABA_A$ receptor sub type.

FIG. 5 shows that androstandiol (0.03-10 µM) enhanced 3 µM GABA-mediated current response at alpha4,beta3, delta receptor. The results are surprising since the potency of androstandiol in the alpha4,beta3,delta subunit composition was 10 times higher than in the alpha1,beta2,gamma2 subunit (FIG. 3: 0.38 µM vs. 3.4 µM).

EXAMPLE 3

Experiments with application of 3beta-hydroxy-5alpha-pregnan-20-one on the $GABA_A$ receptor subtype alpha1, beta2,gamma2 and $GABA_A$ receptor subtype alpha4,beta, delta.

Figure 6:
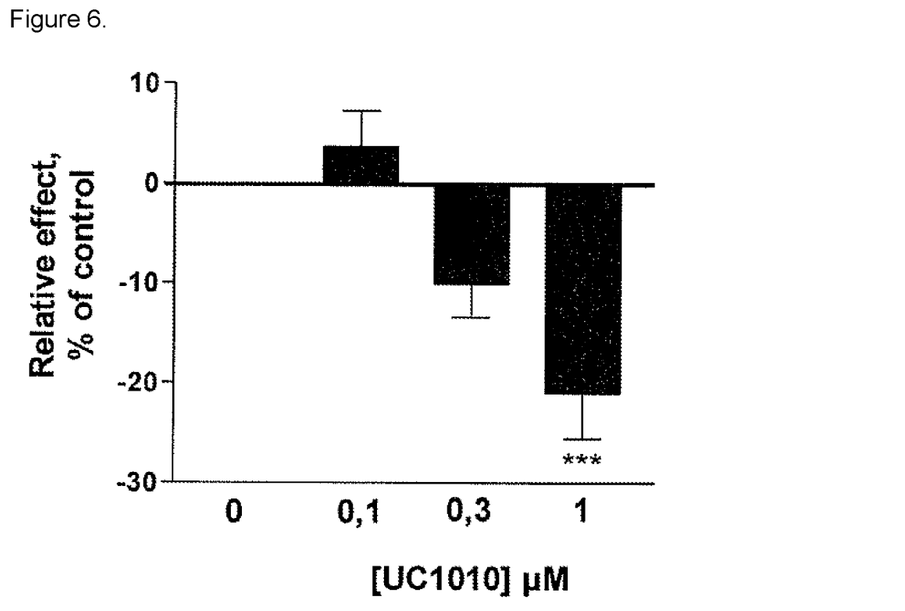
FIG. 6 shows that 3beta-hydroxy-5alpha-pregnan-20-one antagonized the THDOC effect.

Experiments with application on the $GABA_A$ receptor subtype alpha1,beta2,gamma2 showed (a) the inhibitory effect of 3beta-hydroxy-5alpha-pregnan-20-one on the effect of GABA+3alpha-hydroxy-5alpha-pregnan-21-one (THDOC) application at steady state (phasic effect), and (b) effect of 3beta-hydroxy-5alpha-pregnan-20-one on THDOC induced tonic effect (baseline shift). Steroid effect without GABA, steady state and steroid induced baseline shift (without THDOC and GABA), own effect of 3beta-hydroxy-5alpha-pregnan-20-one.

a) In the presence of 30 µM GABA+200 nM THDOC, a single dose of 1 µM 3beta-hydroxy-5alpha-pregnan-20-one antagonized the THDOC enhanced effect by −22.3±5.3% (p<0.001, n=6). In a separate concentration-dependent experiment, 3beta-hydroxy-5alpha-pregnan-20-one in the concentration interval 0.1-1 µM was tested in the presence of 200 nM THDOC and 30 µM GABA. FIG. 6 shows that 3beta-hydroxy-5alpha-pregnan-20-one antagonized the THDOC effect with max −21±4.6% (p<0.001; n=10) which was reached at 1 µM UC1010.

b) The modulatory effect of 1 µM UC1010 in the presence of 30 µM GABA was positive but did not show any significant effect compared to GABA alone (+10.3±7.8%, NS, n=9, data not shown).

TABLE 3

Summary of the results at the receptor alpha1, beta2, gamma2.

| Test | $I_{max}/E_{max}$ | $IC_{50}/EC_{50}$ |
|---|---|---|
| 1-1000 µM GABA | 2600 pA | 3.6 µM |
| 0.03-1 µM THDOC + 30 µM GABA | +115% | 70 nM |
| 1 µM UC1010 + 30 µM GABA | +10.3 ± 7.8% (N.S, n = 9) | — |
| 1 µM UC1010 + 30 µM GABA + 200 nM THDOC | −21 ± 4.6% (P < 0.001, n = 10) | — |
| 0.1-1 µM UC1010 + 30 µM GABA + 200 nM THDOC | −21% | 300 nM |

Table 4 shows application on a $GABA_A$ receptor subtype alpha4,beta,delta: a) GABA application, Steady state; b) the inhibitory effect of 3beta-hydroxy-5alpha-pregnan-20-one on the effect of GABA+3alpha-hydroxy-5alpha-pregnan-21-one (THDOC) application on a $GABA_A$ receptor subtype alpha4,beta,delta at steady state; c) effect on THDOC induced baseline shift, steroid effect without GABA. The THDOC induced baseline shift (without THDOC and GABA) is shown above in Table 1.

TABLE 4

Effect of 1 µM UC1010 on 3 µM GABA, on THDOC ± 3 µM GABA at alpha4, beta3, delta receptor.

| | The effect of 1 µM UC1010 on | Mean ± SEM % (P; N) |
|---|---|---|
| a) | Control 3 µM GABA response (%) | −6.7 ± 3.3% (N = 11, NS) |
| b) | 0.1 µM THDOC + 3 µM GABA (%) | −26 ± 2.4% (N = 13, P = 0.001) |
| c) | 0.1 µM THDOC alone baseline (%) | −43 ± 3.5% (N = 11, P = 0.003) |

Table 5 shows application on a $GABA_A$ receptor subtype alpha1,beta2,gamma2L: a) the inhibitory effect of 3beta-hydroxy-5alpha-pregnan-20-one on the effect of GABA+3alpha-hydroxy-5alpha-androstan-17-ol (3alpha-OH-adiol) application at steady state (phasic effect); b) effect on 3alpha-OH-adiol induced tonic effect (baseline shift); c) Androstandiol effect without GABA is shown in table 2.

TABLE 5

Effect of 1 µM 3beta-hydroxy-5alpha-pregnan-20-one on 8 µM androstandiol ± 30 µM GABA at alpha1, beta2, gamma2.

| The effect of 1 µM UC1010 on | Mean ± SEM % (P; N) |
|---|---|
| a) 8 µM Androstandiol + 30 µM GABA (%) | −30 ± 1.7% (N = 12, P = 0.001) |
| b) 8 µM Androstandiol, baseline shift (%) | −33 ± 7.6% (N = 8, P = 0.012) |

Maximal modulatory effect of 1 µM 3beta-hydroxy-5alpha-pregnan-20-one in presence of 30 µM GABA alone was not significant (10.3±7.8%, NS, n=9). This shows that 1 µM 3beta-hydroxy-5alpha-pregnan-20-one had no effect of GABA itself, therefore no further studies with UC1010 and GABA alone was done.

Table 6 shows application on a $GABA_A$ receptor subtype alpha4,beta,delta: a) effect on 3alpha-OH-adiol induced baseline shift; b) the inhibitory effect of 3beta-hydroxy-5alpha-pregnan-20-one on the effect of GABA+3alpha-OH-adiol application on a $GABA_A$ receptor subtype alpha4,beta,delta at steady state; c) Androstandiol effect without GABA is shown below in table 7.

TABLE 6

Effect of 1 µM UC1010 on 3 µM GABA, on androstandiol + 3 µM GABA at alpha4, beta3, delta.

| The effect of 1 µM UC1010 on | Mean ± SEM % (P; N) |
|---|---|
| a) 3 µM GABA response (%) | −6.7 ± 3.3% (N = 11, NS) |
| b) 0.6 µM Androstandiol + 3 µM GABA (%) | −18 ± 2.0% (N = 9, P = 0.008) |
| b) 0.8 µM Androstandiol + 3 µM GABA(%) | −22 ± 2.6% (N = 6, P = 0.028) |

TABLE 7

Androstandiol 3 µM and 10 µM significantly induce current response in absence of GABA at alpha4, beta3, delta receptor.

| Androstandiol (µM) Baselineshift | Mean ± SEM pA (N; P) |
|---|---|
| 3 | +8 ± 3.6 pA (N = 11; P = 0.004) |
| 10 | +13 ± 4.8 pA (N = 12; P = 0.000) |

Androstandiol (3 µM and 10 µM) had a significant but minor effect on current response in absence of GABA compare to baseline, current response at EC-solution (Table 7). Androstandiol induced current response was so low that the effect of 1 µM UC1010 on the baseline shift was not possible to study.

Finally, 1 µM 3beta-hydroxy-5alpha-pregnan-20-one had no effect by itself at the alpha4,beta3,delta $GABA_A$ receptor by itself, −0.4±0.3 pA (N=11, NS) compare to current response at EC solution (−0.1±0.3 pA; N=10).

Conclusions

The present invention thus surprising provides a possible treatment of essential tremor as 3beta-hydroxy-5alpha-pregnan-20-one is active as a $GABA_A$ steroid modulator antagonist and thus can block the enhancement that the $GABA_A$ receptor modulating steroids induce in the main receptor subtypes located in thalamus of patients with essential tremor.

1 µM 3beta-hydroxy-5alpha-pregnan-20-one acted as an antagonist to both androstandiol and to THDOC. 3beta-hydroxy-5alpha-pregnan-20-one significantly reduced the THDOC and androstandiol enhanced GABA mediated effect both at alpha1,beta2,gamma2 and at alpha4,beta3,delta $GABA_A$ receptor subtypes. Further, 1 µM 3beta-hydroxy-5alpha-pregnan-20-one significantly reduced the THDOC enhanced GABA mediated current response without any effect on GABA at alpha4,beta3,delta $GABA_A$ receptor subtype. 1 µM 3beta-hydroxy-5alpha-pregnan-20-one alone had no effect at the alpha4,beta3,delta $GABA_A$ receptor subtype.

Androstandiol enhanced the GABA mediated current response at both alpha1,beta2,gamma2 and alpha4,beta3,delta $GABA_A$ receptor subtypes. However, the $EC_{50}$ and $E_{max}$ differed between the subtypes. At the alpha1,beta2,gamma2 receptor the androstandiol $EC_{50}$ was 3.4 µM compared to 0.38 µM on alpha4,beta3,delta. Also, $E_{max}$ at the alpha1,beta2,gamma2 was 281% compared to $E_{max}$=142% at alpha4,beta3,delta. This provides that androstandiol was more efficient but less potent at the alpha1,beta2,gamma2 receptor compare to alpha4,beta3,delta receptor.

THDOC enhanced the GABA mediated current response at alpha4,beta3,delta $GABA_A$ receptor, where the $EC_{50}$ was 47 nM and $E_{max}$ was 297%. This provides that THDOC was more efficient and more potent at alpha4,beta3,delta $GABA_A$ receptor compared to androstandiol.

The invention claimed is:

1. A method of treating essential tremor in a patient, comprising administering an effective amount of 3beta-hydroxy-5alpha-pregnan-20-one, to the patient.

2. The method of claim 1, wherein the 3beta-hydroxy-5alpha-pregnan-20-one-is administered in combination with at least one additional active compound, selected from the group consisting of primidone, topiramate, phenobarbital, propranolol, atenolol, nadolol, metoprolol, timolol, R-baclofen, clonazepam, gabapentin, pregabalin, nimodipine, clozapine, olanzapine, and botulinim toxin A.

3. The method of claim 1, further comprising the step of administering deep brain stimulation to the patient.

4. The method of claim 2, further comprising the step of administering deep brain stimulation to the patient.

5. The method of claim 1, wherein the 3beta-hydroxy-5alpha-pregnan-20-one is in the form of a pharmaceutically acceptable ester.

6. The method according to claim 1, wherein said 3beta-hydroxy-5-alpha-pregnan-20-one is administered intravenously, nasally, buccally, vaginally, rectally, subcutaneously, percutaneously or orally.

7. The method according to claim 1, wherein said 3beta-hydroxy-5-alpha-pregnan-20-one is administered topically, locally, orally, parenterally or pulmonary.

* * * * *

UNITED STATES PATENT AND TRADEMARK OFFICE
CERTIFICATE OF CORRECTION

Page 1 of 1

PATENT NO. : 11,026,953 B2
APPLICATION NO. : 16/484920
DATED : June 8, 2021
INVENTOR(S) : Bäckström et al.

It is certified that error appears in the above-identified patent and that said Letters Patent is hereby corrected as shown below:

On the Title Page

Item (22) should read:
PCT Filed: Feb. 9, 2018

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*